(12) United States Patent
Rahman

(10) Patent No.: US 8,596,110 B2
(45) Date of Patent: Dec. 3, 2013

(54) DEVICE AND METHOD FOR TESTING REVERSE OSMOSIS MEMBRANES

(75) Inventor: Faizur Rahman, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 379 days.

(21) Appl. No.: 13/047,566

(22) Filed: Mar. 14, 2011

(65) Prior Publication Data

US 2012/0234083 A1    Sep. 20, 2012

(51) Int. Cl.
*G01N 15/08* (2006.01)

(52) U.S. Cl.
USPC .............................................. 73/38; 73/64.47

(58) Field of Classification Search
USPC ............................. 73/64.47, 38, 61.73, 61.63
See application file for complete search history.

(56) References Cited

U.S. PATENT DOCUMENTS

| | | | |
|---|---|---|---|
| 4,137,756 A * | 2/1979 | Cosack et al. | ............... 73/64.47 |
| 4,188,817 A | 2/1980 | Steigelmann | |
| 4,468,951 A * | 9/1984 | Garcia et al. | ....................... 73/38 |
| 5,905,197 A | 5/1999 | Wilf | |
| 6,007,710 A | 12/1999 | Pavel | |
| 6,324,898 B1 | 12/2001 | Cote et al. | |
| 7,584,061 B2 | 9/2009 | Wilf et al. | |
| 8,424,367 B2 * | 4/2013 | Ploehn et al. | ....................... 73/38 |
| 2005/0229679 A1 * | 10/2005 | Gupta et al. | ....................... 73/38 |
| 2008/0289403 A1 | 11/2008 | Palacios Donaque | |
| 2009/0320563 A1 | 12/2009 | Wilf et al. | |

FOREIGN PATENT DOCUMENTS

| | | | |
|---|---|---|---|
| CN | 101013077 A | | 8/2007 |
| JP | 55097286 A | * | 7/1980 |
| JP | 10015059 A | | 1/1998 |
| JP | 2005195499 A | | 7/2005 |
| WO | WO9813682 A1 | | 4/1998 |
| WO | WO2008142190 A1 | | 11/2008 |

OTHER PUBLICATIONS

F. Rahman and M. Skyllas-Kazacos, "Optimization of Supersaturated Vanadium Electrolyte for High Energy Density Vanadium Redox Battery", 4th International Conference and Exhibition on Chemistry in Industry, Bahrain, Oct. 30-Nov. 1, 2000.

* cited by examiner

*Primary Examiner* — Hezron E Williams
*Assistant Examiner* — Paul West
(74) *Attorney, Agent, or Firm* — Richard C. Litman

(57) ABSTRACT

The device for testing reverse osmosis membranes provides for the quick and efficient testing of the transport properties of reverse osmosis membranes at a fixed pressure over a fixed period of time. The device includes a first chamber adapted for receiving a volume of de-ionized water and a second chamber adapted for receiving a volume of brine. In use, a reverse osmosis membrane to be tested is clamped between the first and second chambers and a pressurized inert gas, such as gaseous nitrogen, is injected into the second chamber at known pressure to initiate reverse osmosis transport. The transport is carried out at the known pressure for a fixed period of time, after which the concentration of brine volume of water in the first chamber is measured.

2 Claims, 4 Drawing Sheets

DEVICE AND METHOD FOR TESTING REVERSE OSMOSIS MEMBRANES

BACKGROUND OF THE INVENTION

1. Field of the Invention

The present invention relates generally to laboratory testing of reverse osmosis apparatus, and particularly to a device and method for testing reverse osmosis membranes that provides a static diffusion cell for measurement of the efficiency of flat membranes used for reverse osmosis.

2. Description of the Related Art

Reverse osmosis (RO) is a method that removes many types of large molecules and ions from solutions by applying necessary pressure to the solution when it is on one side of a selectively permeable membrane to reverse the normal osmotic process. The result is that the solute is retained on the pressurized side of the membrane and the pure solvent is allowed to pass to the other side. In order to be "selective", the membrane should not allow large molecules or ions through its pores, but should allow smaller components of the solution, such as the solvent, to pass freely.

In the normal osmosis process, the solvent naturally moves from an area of low solute concentration through a membrane to an area of high solute concentration. At equilibrium, the concentration of the solute is equal on both sides of the membrane. The movement of a pure solvent to equalize solute concentrations on each side of a membrane generates a pressure, and this is the "osmotic pressure". Applying an external pressure to reverse the natural flow of pure solvent, thus, is "reverse osmosis". The process is similar to membrane filtration. However, it should be noted that there are key differences between reverse osmosis and filtration. The predominant removal mechanism in membrane filtration is straining, or size exclusion, so the process can theoretically achieve perfect exclusion of particles regardless of operational parameters such as influent pressure and concentration. Reverse osmosis, however, involves a diffusive mechanism so that separation efficiency depends upon solute concentration, pressure, and water flux rate. Reverse osmosis is most commonly known for its use in desalination processes to provide drinking water purification from seawater, removing the salt and other substances from the water molecules.

In reverse osmosis, pressure is applied to a compartment with high concentration. In this case, there are two forces influencing the movement of water: the pressure caused by the difference in solute concentration between the two compartments (i.e., the osmotic pressure) and the externally applied pressure. FIG. 4 diagrammatically illustrates a conventional reverse osmosis process of the type typically used in desalination. In system 100, seawater SW1 flows under pressure (generated by a high pressure pump 102) into a reverse osmosis unit 106 (with a reverse osmosis membrane mounted therein). Seawater SW1 is also drawn into a pressure exchanger 108.

Filtration within the reverse osmosis unit 106 generates both fresh water FW to be extracted, and also the waste concentrate flow CF, which is also pushed, under pressure, through the pressure exchanger 108. Waste concentrate is extracted and removed through concentrate drain CD, and now pressurized, mixed seawater SW2 is drawn by circulation pump 104 and injected back through the reverse osmosis unit 106.

Because reverse osmosis filtration is used in the production of drinking water and for other purposes in which purity and efficiency is critical, constant testing of the reverse osmosis membranes themselves is necessary. Particularly, in the field of desalination, salt rejection, scaling and fouling are all critical factors to be tested. Salt rejection is typically presented as a percentage, calculated as 100×[1−(product concentration/feed concentration)]. Scaling is the precipitation and deposition of scale forming compounds on the membrane surface when the brine is concentrated. Fouling is the deposition or accumulation of contaminants on the membrane surface.

Typical testing occurs dynamically in actual reverse osmosis processes, which are often performed in large-scale plants (particularly in desalination processes), thus requiring a great deal of effort. It would be desirable to provide small scale testing which is relatively quick and easy and provides highly accurate results.

Thus, a device and method for testing reverse osmosis membranes solving the aforementioned problems is desired.

SUMMARY OF THE INVENTION

The device for testing reverse osmosis membranes provides for the quick and efficient testing of the transport properties of reverse osmosis membranes at a fixed pressure over a fixed period of time. The device includes a first chamber having a first housing, the first housing having at least one wall defining a first reservoir adapted for receiving a volume of de-ionized water. The first housing has an open proximal end and a first frame mounted thereto, bordering the open proximal end thereof. A second chamber is further provided having a second housing. The second housing similarly has at least one wall defining a second reservoir adapted for receiving a volume of brine. The second housing also has an open proximal end and a second frame mounted thereto, bordering the open proximal end thereof.

In use, a reverse osmosis membrane to be tested is releasably clamped between the first and second frames so that the open proximal end of the first housing is positioned against a first surface of the reverse osmosis membrane and the open proximal end of the second housing is positioned against an opposed second surface of the reverse osmosis membrane. Preferably, a porous membrane support is sandwiched between the first frame of the first housing and the reverse osmosis membrane to stabilize and support the reverse osmosis membrane during testing.

In order to maintain the known pressure during testing, a first gasket is preferably sandwiched between the first frame and the porous membrane support, and a second gasket is similarly preferably sandwiched between the second frame and the reverse osmosis membrane. A pressurized inert gas, such as gaseous nitrogen, is injected into the second chamber at known pressure to initiate the reverse osmosis transport. The transport is carried out at the known pressure for a fixed period of time, after which the concentration and volume of brine in the first chamber is measured, and the concentration and volume of pure water in the second chamber is measured. These measurements allow for determination of salt rejection and permeate flux associated with the reverse osmosis membrane being tested.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
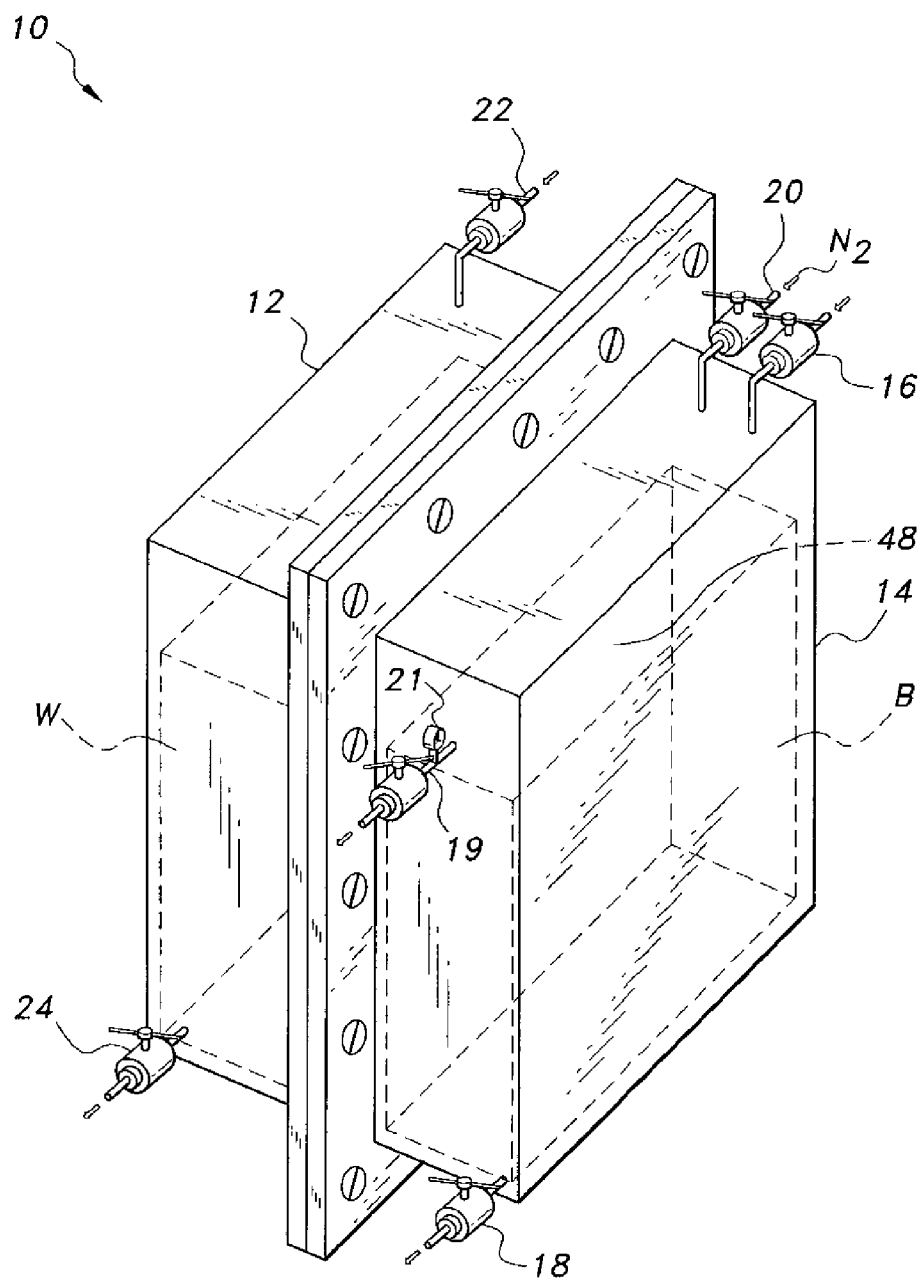
FIG. 1 is a perspective view of a device for testing reverse osmosis membranes according to the present invention.
Figure 2:
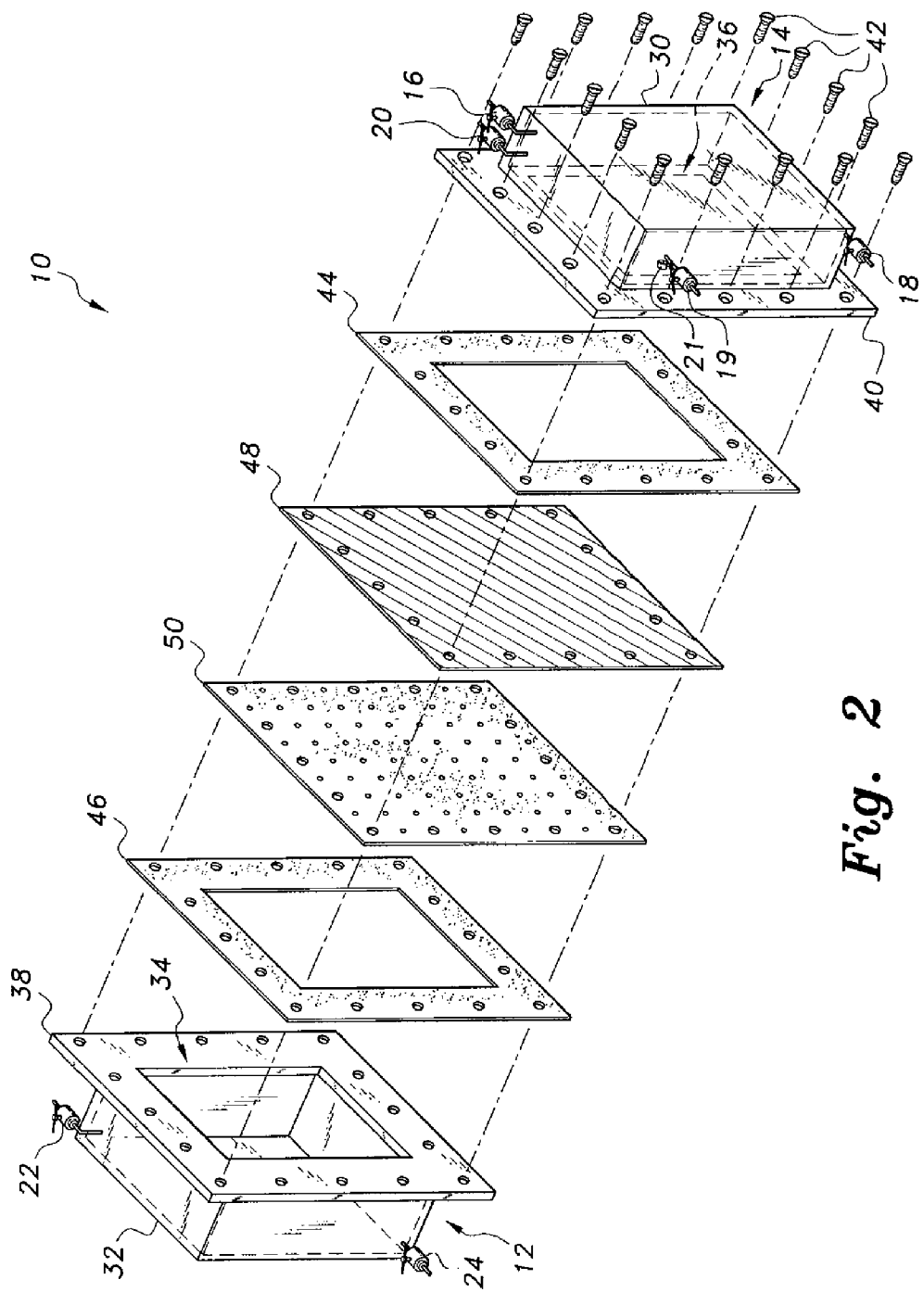
FIG. 2 is an exploded perspective view of the device for testing reverse osmosis membranes of FIG. 1.

Referring now to FIGS. 1 and 2, the device 10 for testing reverse osmosis membranes provides a static diffusion cell for the quick and efficient testing of the transport properties of reverse osmosis membranes at a fixed pressure over a fixed period of time. The device 10 includes a first chamber 12 having a first housing 32, the first housing 32 having at least one wall defining a first reservoir adapted for receiving a volume of de-ionized water W. Preferably, the first housing 32 is formed from an optically transparent material, allowing for direct optical measurements of volume and fluid concentration to be made through the at least one wall. As best shown in FIG. 2, the first housing 32 has an open proximal end 34 and has a first flange or frame 38 mounted thereto bordering the open proximal end 34.

Similarly, a second chamber 14 has a second housing 30. The second housing 30 similarly has at least one wall defining a second reservoir adapted for receiving a volume of brine B. The second housing 30 also has an open proximal end 36 and a second flange or frame 40 mounted thereto bordering the open proximal end 36.

The first housing has an inlet port 22 formed therethrough, the inlet port 22 having a suitable valve for selective injection of the volume of de-ionized water W into the first housing 32. Prior to testing the reverse osmosis membrane, the volume of de-ionized water W is fixed at a known volume and is pure de-ionized water. The first housing 32 also has an outlet port 24, the outlet port 24 having a suitable valve for selective release of fluids from within first chamber 12, allowing fluid concentrations to be measured following testing. The volume of fluids contained within the first chamber 12 following testing may also be measured following release of the fluids through the outlet port 24.

Similarly, the second housing has a brine inlet port 16 formed therethrough, the inlet port 16 having a suitable valve for selective injection of the volume of brine B into second housing 30. Prior to testing of the reverse osmosis membrane, the volume of brine B is fixed at a known volume and the salt concentration thereof is known. A gas inlet port 20 is further provided for selective injection of a pressurized inert gas, such as gaseous diatomic nitrogen, into the second chamber 14. A gas outlet port 19 is similarly provided (as shown in FIG. 1, the inlet port 20 and the outlet port 19 are preferably positioned above the desired brine level) to allow for the selective removal of pressurized gas from within second chamber 14. A pressure gauge 21 may be mounted within the outlet port 19, allowing for the selective control of the pressure of the gas within second chamber 14 through selective and measured release thereof to regulate the pressure. The second housing 30 also has a brine outlet port 18, the outlet port 18 having a suitable valve for selective release of fluids from within second chamber 14, allowing fluid concentrations to be measured following testing. The volume of fluids contained within second chamber 14 following testing may also be measured following release of the fluids through the brine outlet port 18.

In use, a flat reverse osmosis membrane 48 to be tested is releasably clamped between the first and second flanges or frames 38, 40 so that the open proximal end 34 of the first housing 32 is positioned adjacent a first surface of the reverse osmosis membrane 48, and the open proximal end 36 of the second housing 30 is positioned adjacent an opposed second surface of the reverse osmosis membrane 48. Preferably, a porous membrane support 50 is sandwiched between the first frame 38 of the first housing 32 and the reverse osmosis membrane 48, as shown in FIG. 2, to stabilize and support the reverse osmosis membrane 48 during testing.

In order to maintain the known pressure during testing, a first gasket 46 is preferably sandwiched between the first frame 38 and the porous membrane support 50, as shown in FIG. 2, and a second gasket 44 is similarly preferably sandwiched between the second frame 40 and the reverse osmosis membrane 48. Any suitable type of releasable fastener, such as exemplary screws 42, may be used to clamp together the first chamber 12, the first gasket 46, the membrane support 50, the reverse osmosis membrane 48, the second gasket 44, and the second chamber 14 in a fluid-tight fashion.

Figure 3:
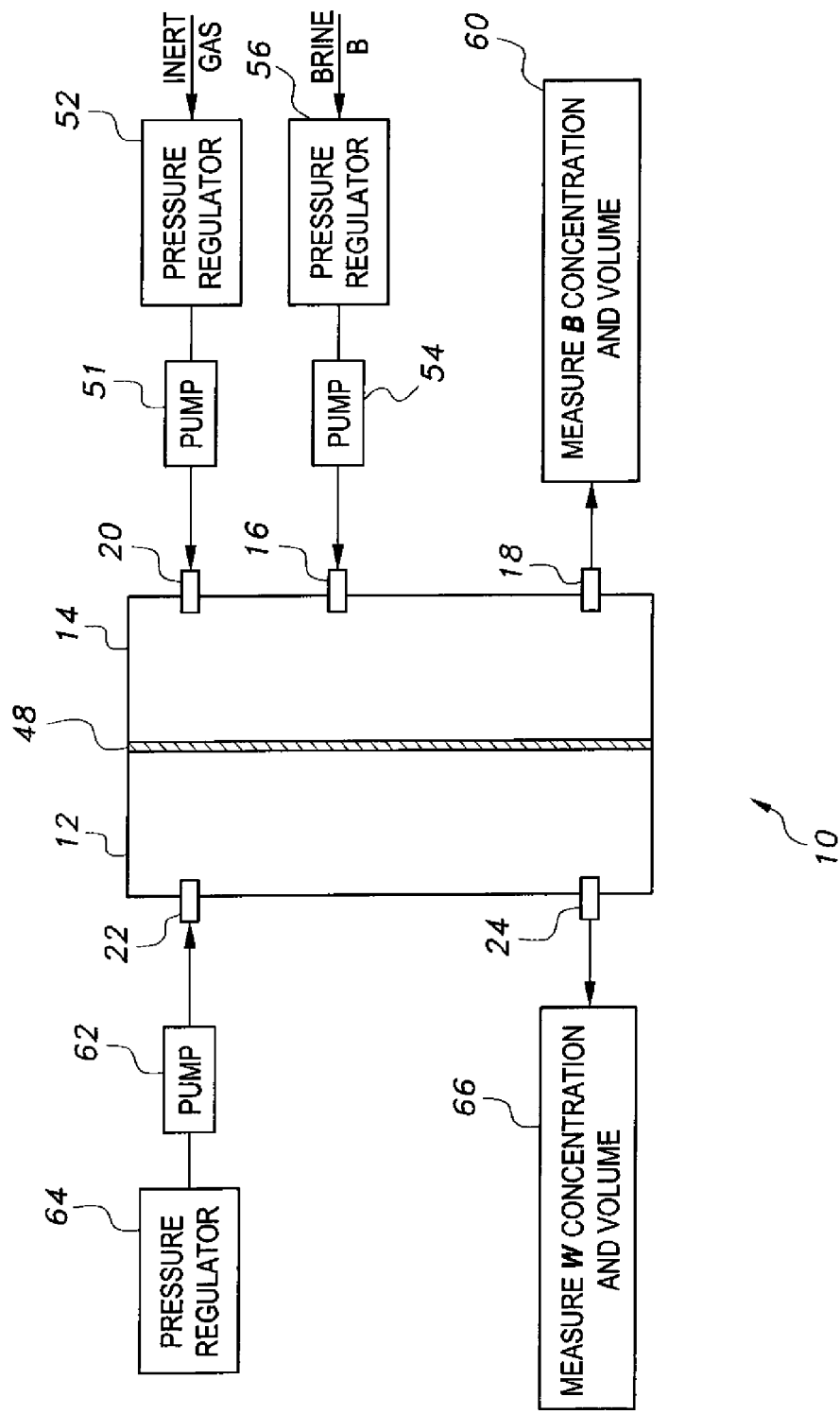
FIG. 3 is a diagrammatic illustration of the device for testing reverse osmosis membranes of FIG. 1.
Figure 4:
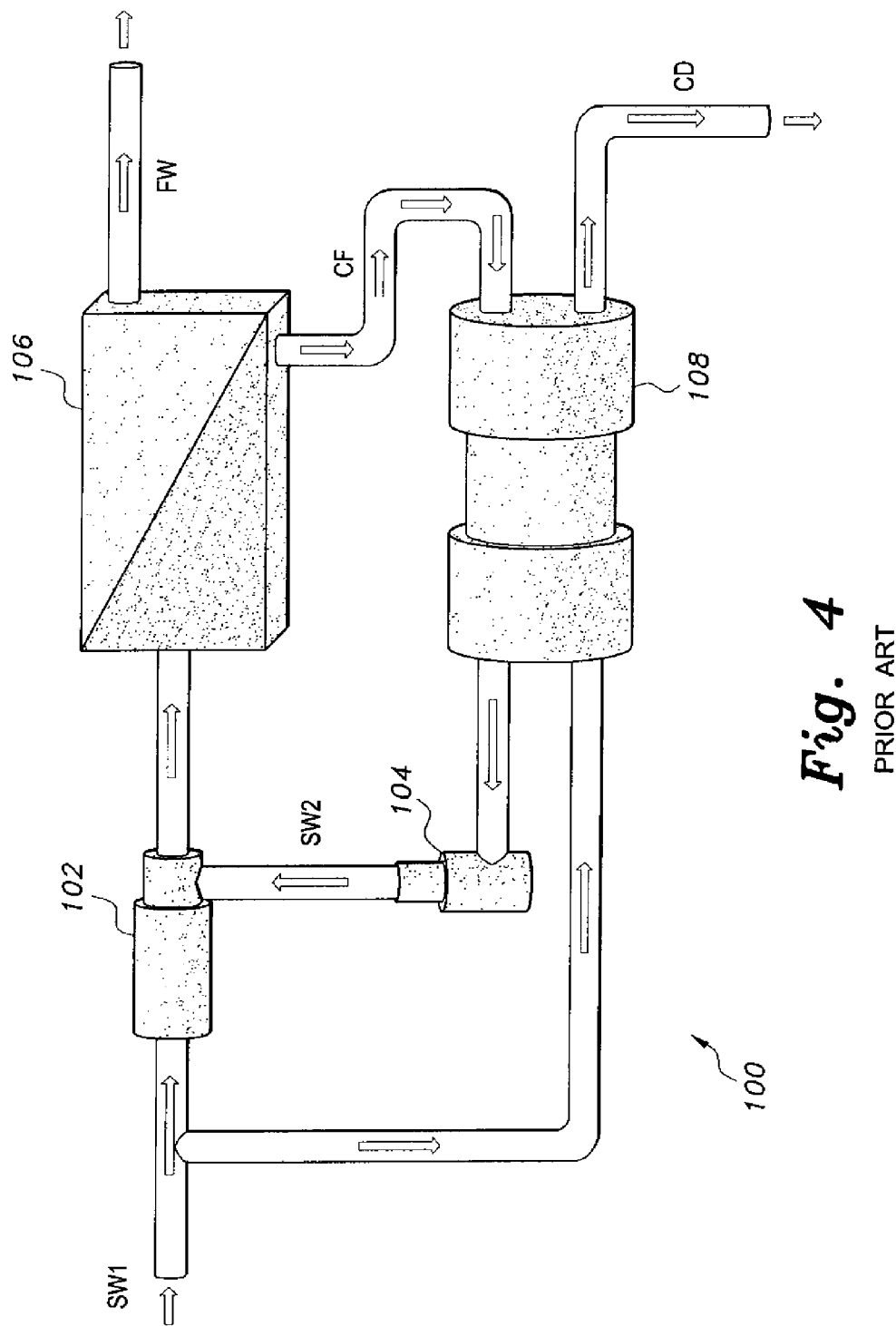
FIG. 4 diagrammatically illustrates a prior art reverse osmosis transport device.

As diagrammatically illustrated in FIG. 3, brine B (i.e., feed water) may be injected into the second chamber 14 by any suitable type of pump 54 or the like, and the pressure and/or volume thereof may be measured and regulated by an associated regulator 56. The volume of the brine B may also be measured directly through the transparent wall of housing 30. Then, a pressurized inert gas, such as gaseous diatomic nitrogen, is injected into the second chamber 14, through the inlet port 20 at known pressure to initiate the reverse osmosis transport. The transport is carried out at the known pressure for a fixed period of time, after which the concentration and volume of brine in the first chamber 12 is measured, and the concentration and volume of pure water in the second chamber 14 is measured. These measurements allow for determination of salt rejection and permeate flux associated with the reverse osmosis membrane 48 being tested.

It should be understood that any suitable type of pump 51 or the like may be utilized for injection of the pressurized inert gas into second chamber 14. Inert gas can also be injected in the chamber 14 through a pressurized inert gas cylinder. The pressure thereof may be measured and regulated by the gauge 21 at the outlet control valve 19, or may be regulated at the point of injection through a pressure regulator 52 associated with the pump 51. Care must be taken to maintain the level of brine B above the membrane during the operation of the test cell.

Similarly, it should be understood that any suitable type of pump 62 or the like may be utilized for injection of the de-ionized pure water into first chamber 12. The pressure and/or volume thereof may be measured and regulated by an associated regulator 64. The volume of the de-ionized water W may also be measured directly through the transparent wall of housing 32.

Devices and devices for volumetric and liquid concentration measurements are well known in the art. It should be understood that any suitable type of detector, sensor or other device or any known procedure for measuring the concentration and volume of pure water 66 may be used for determination of the concentration and volume of pure water expelled from outlet 24 of first chamber 12 following the reverse osmosis transport at the fixed time at fixed pressure.

Similarly, it should be further understood that any suitable type of detector, sensor or other device or any known procedure for measuring the concentration and volume of brine 60 may be used for determination of the concentration and volume of brine expelled from the outlet 18 of the second chamber 14 following the reverse osmosis transport at the fixed time at fixed pressure. It should be noted that the first chamber only contains pure water and the second chamber only contains brine.

The device 10, which may be termed a static diffusion cell, permits flat, semipermeable membranes used for reverse osmosis to be tested statically at low pressures in the laboratory with precisely known concentrations of brine and precisely regulated pressures, rather than dynamically while in use in the reverse osmosis apparatus itself.

It is to be understood that the present invention is not limited to the embodiments described above, but encompasses any and all embodiments within the scope of the following claims.

I claim:

1. A method for testing reverse osmosis membranes, comprising the steps of:
   partially filling a first chamber with a known volume of de-ionized water;
   partially filling a second chamber with a known volume of brine of known concentration;
   clamping a flat reverse osmosis membrane to be tested between the first and second chambers so that an open end of the first chamber is positioned against a first surface of the reverse osmosis membrane and an open end of the second chamber is positioned against an opposed second surface of the reverse osmosis membrane;
   injecting a pressurized inert gas at a known pressure into the second chamber to initiate a reverse osmosis transfer through the reverse osmosis membrane;
   measuring the concentration of brine in the first chamber at a measured period of time after initiation of reverse osmosis to determine salt rejection by the membrane; and
   measuring the volume of pure water in the first chamber at a measured period of time after initiation of reverse osmosis to determine flow rate through the reverse osmosis membrane.

2. The method for testing reverse osmosis membranes as recited in claim 1, further comprising the step of monitoring pressure in the second chamber during said step of measuring the volume of pure water to determine the flow rate through the membrane at the pressure in the second chamber.

* * * * *